US 6,638,554 B1

(12) United States Patent
Rubio et al.

(10) Patent No.: US 6,638,554 B1
(45) Date of Patent: Oct. 28, 2003

(54) CONTINUOUS PRODUCTION OF AN INSTANT CORN FLOUR FOR AREPA AND TORTILLA, USING AN ENZYMATIC PRECOOKING

(75) Inventors: Manuel J. Rubio, Miami Beach, FL (US); Roberto Contreras, Guadalupe (MX); Felipe Rubio, Edinburg, TX (US)

(73) Assignee: Roberto Gonzalez Barrera, Guadalupe (MX)

( * ) Notice: Subject to any disclaimer, the term of this patent is extended or adjusted under 35 U.S.C. 154(b) by 0 days.

(21) Appl. No.: 10/231,291

(22) Filed: Aug. 30, 2002

(51) Int. Cl.[7] .................................................. A23L 1/00
(52) U.S. Cl. ...................... 426/508; 426/463; 426/464; 426/622; 426/626
(58) Field of Search ................... 426/507, 509, 426/463, 464, 481, 518, 622, 626, 18, 52

(56) References Cited

U.S. PATENT DOCUMENTS

| | | |
|---|---|---|
| 2,584,893 A | 2/1952 | Lloyd et al. |
| 2,704,257 A | 3/1955 | Diez de Sollano et al. |
| 4,513,018 A | 4/1985 | Rubio |
| 4,594,260 A | 6/1986 | Vaqueiro et al. |
| 4,990,343 A | 2/1991 | Haarasilta et al. |
| 5,176,931 A | 1/1993 | Herbster |
| 5,447,742 A | 9/1995 | Malvido et al. |
| 5,532,013 A | 7/1996 | Martinez-Bustos et al. |
| 5,558,898 A | 9/1996 | Sunderland |
| 5,698,245 A | 12/1997 | Tanaka et al. |
| 6,025,011 A | 2/2000 | Wilkinson et al. |
| 6,066,356 A | 5/2000 | Van Der Wouw et al. |
| 6,068,873 A | 5/2000 | Delrue et al. |
| 6,265,013 B1 | 7/2001 | Martinez-Montes et al. |
| 6,322,836 B1 | 11/2001 | Rubio et al. |
| 6,326,045 B1 | 12/2001 | Rubio et al. |
| 6,344,228 B1 | 2/2002 | Rubio et al. |
| 6,387,437 B1 | 5/2002 | Martinez-Bustos et al. |
| 6,428,828 B1 | 8/2002 | Jackson et al. |
| 2002/0102326 A1 | 8/2002 | Rubio et al. |

FOREIGN PATENT DOCUMENTS

| | | |
|---|---|---|
| WO | 00/45647 | 8/2000 |
| WO | 01/98509 A2 | 12/2001 |

OTHER PUBLICATIONS

Mario M. Alvarez et al., "Biodegradative Treatment of Nixtamalization Wastewaters (NEJAYOTE), Using Mobilized Native Mixed Cultures in Anoxic Environments," Abstract in Keystone Symposia of Environmental Biotechnology, *Journal of Cellular Biochemistry*, 1995.

Cory M. Bryant et al., "Effect of Lime on Gelatinization of Corn Flour and Starch," *Cereal Chem.*, V. 74, 1997, pp. 171–175.

Roberto Cuevas et al., "The Technology for Industrial Production of Precooked Corn Flour in Venezuela," *Cereal Foods World*, V. 30, 1985, pp. 707–712.

(List continued on next page.)

*Primary Examiner*—George C. Yeung
(74) *Attorney, Agent, or Firm*—Young & Thompson

(57) ABSTRACT

Precooked and partially-debranned corn flour is continuously produced by an enzymatic precooking using a commercial xylanase as a processing aid. The low-temperature and near neutral-pH precooking with a xylanase effected a partial bran hydrolysis while avoiding excessive pregelatinization, reduced washing, and corn solid loss in wastewater. Moisture content is then stabilized, followed by milling and drying at a high-temperature and short-time to produce a controlled gelatinization in the ground kernel, cooling and further drying the dried-ground particle. A fine particle size or flour is separated and recovered from the coarser particle which is also segregated to partially isolate a bran fraction for animal feed or integral flour, remilling and sieving the coarser particle to produce an instant corn flour for arepa, and admixing the fine particle with lime to obtain a masa flour for tortilla and other snack foods.

15 Claims, 1 Drawing Sheet

OTHER PUBLICATIONS

"Enzymes Used in Food Processing (as compiled by the ETA Members)," Table, FCC List, Enzyme Technical Association, 2002, pp. 1–7, (www.enzymetechnicalassoc.org).

"Partial List of Enzyme Preparations that are Used in Foods," U.S. Food and Drug Administration, Center for Food Safety & Applied Nutrition, Office of Food Additve Safety, Jul. 2001, pp. 1–4 (www.cfsan.fda.gov).

"Summary of All GRAS Notices," U.S. Food and Drug Administration, Center for Food Safety & Applied Nutrition, Office of Food Additive Safety, Oct. 2002, pp. 1–6.

W.W. Leung, et al., "Food Composition Table for Use in Latin America," Research Project sponsored jointly by The Institute of Nutrition of Central America & Panama, Guatemala City, C.A.; and The Interdepartmental Committee on Nutrition for National Defense, National Institutes of Health, U.S.A., 1961, pp. 12–15.

Ricardo Martinez et al., "Kinetic Approach to Nixtamalization of Corn Pericarp," *Cereal Chem.*, V. 78, 2001, pp. 107–110.

P.R. Mathewson, Enzymes, An Eagan Press Handbook Series, 1998, American Association of Cereal Chemists, Inc., pp. 15–19, 91, and 93–95.

D. Sahai et al., "A Novel Enzymatic Nixtamalization Process for Producing Corn Masa Flour," *Cereal Foods World*, V. 46, pp. 240–245.

Luc Saulnier et al, "Cell Wall Polysaccharide Interactions in Maize Bran," *Carbohydrate Polymers*, V. 26, 1995, pp. 279–287.

R. Bressani, "Nutritional Quality of Nixtamilized Corn Mesa Flour, Achievement Through Fortification with Micronutrients," SUSTAIN (Sharing United States Technology to Aid in he Improved of Nutrition), "Fortification of Corn Masa Flour with Iron and/or Other Nutrients: A Literature and Industry Experience Review," 1997, pp. 34, 37–38, 46, 49 and 61.-

CONTINUOUS PRODUCTION OF AN INSTANT CORN FLOUR FOR AREPA AND TORTILLA, USING AN ENZYMATIC PRECOOKING

BACKGROUND OF INVENTION

1. Field of the Invention

The present invention relates to a method of low-temperature and near neutral-pH precooking for the production of corn flour and, more particularly, to one that achieves continuous partial hydrolysis of the corn insoluble fiber and avoids excessive pregelatinization with a xylanase as a processing aid during the manufacture of an instant corn flour for the elaboration of arepa and tortilla and derivatives.

2. Description of Related Art

The production of high-quality masa flour can be produced by conventional techniques only if the food-grade dent corn has the following characteristics: uniformity in kernel size and hardness, low number of stress-cracks and kernel damage and ease of pericarp removal during the lime-water cooking process. The mature kernel has four separable components, on a dry weight basis: tip cap (0.8–1.1%), pericarp or bran (5.1–5.7%), endosperm (81.1–83.5%), and germ (10.2–11.9%). In dry or wet-milling processes the bran includes the pericarp, tip cap, aleurone layer and adhering pieces of starchy endosperm as well. Nixtamalized corn flour (NCF) is produced by the steps of alkaline cooking of corn, washing, milling the nixtamal and drying to give corn masa flour. This flour is sieved and blended for different product applications and it is usually supplemented with additives before packaging for commercial table or packaged-tortilla and snack production. Although the pericarp or bran is partially removed during the alkaline-cooking and washing process stages, there is still fiber left from the corn kernel (Montemayor and Rubio, 1983, U.S. Pat. No. 4,513,018). Whole Nixtamalized corn flour or masa flour can contain from 7–9% of total dietary fiber or bran with 6–8% mainly consisting of insoluble fiber on a dry basis (Sustain, 1997).

The cell walls or non-starch polysaccharides (NSP) are the major corn dietary fiber components and are composed of hemicellulose (heteroxylan or pentosan and β-glucan: 4.4–6.2%), cellulose (2.5–3.3%) and some lignin (0.2%). According to Watson (1987: Tables IV and VII), the corn pericarp makes up 5–6% of the kernel dry weight. This pericarp also contains 90% insoluble fiber (67% hemicellulose and 23% cellulose) and only 0.6% soluble-fiber (soluble-arabinoxylan and β-glucan). It is estimated that dietary fiber in both pericarp or bran (4.9%) and endosperm (2.6%) make up 80% of the total dietary fiber. The corn insoluble fiber is mainly found in the pericarp and endosperm (aleurone and starchy) which make up 68% of the total dietary fiber (9.5% in a dry-weight basis).

Unlike corn endosperm, in which soluble fiber amounts to 12% of the total fiber (4.1%), in whole wheat, soluble fiber represents 22% of total fiber (about 20% of the flour water-uptake is bound to the soluble pentosan fraction). Arabinoxylan is a complex polymer (20,000–170,000 Daltons) with a linear backbone of (1,4)-β-xylopiranosyl units to which substituents are attached through O2 and O3 atoms of the xylosil residues (mainly, α-L-arabinofuranosyl). This polymer is apparently linked to the cellulose skeleton in the corn cell wall by ester linkage cross-bonding through ferulic and diferulic acid (Watson, 1987). However, heteroxylan insolubility in corn bran might be due to protein-polysaccharide linkages and a highly branched structure (23% of the xylan backbone does not bear side-chains) as opposed to wheat bran (Saulnier et al., 1995).

During alkali-cooking and/or steeping, there are chemical and physical changes such as nutrient losses along with partial pericarp or bran removal, degradation of the endosperm periphery with starch gelatinization/swelling and protein denaturation in the precooked corn kernel. The most important nutritional modifications are: an increase in the calcium level with improvement in the Ca to P ratio, a decrease in insoluble dietary fiber and zein-protein, a reduction in thiamin and riboflavin, an improvement of the leucine to isoleucine ratio reducing the requirement for niacin, and leaching the aflatoxins into the wastewater (Sustain, 1997).

The known cooking methods (batch or continuous) have been proposed as the critical variables (Sahai et al., 2001) which determine soluble-solid loss (1% to 1.6% COD) in limewater residue for anaerobic biodegradation (Alvarez and Ramirez, 1995). Dry solid matter (1.5%-2.5%) includes an average of 50–60% dietary fiber, 15–20% ash, 15% starch, 5–10% protein and 5% fat. Bryant et al., (1997) showed an optimum change in starch behavior at a lime level similar to the corn masa industry where starch gelatinization indicators (enzyme digestion, water retention capacity, starch solubility and DSC-peak temperature=69° to 75° C.) are increased with lime addition of 0 to 0.4%, peaking at 0.2%. They also found a peak-viscosity temperature reduction upon the addition of lime up to 0.5%, indicating faster granule swelling that requires less thermal energy. Corn pericarp nixtamalization (Martinez et al., 2001) has a first-order stage associated with a fast dissolution of hot-water soluble fractions as starch and pectin, and alkali-soluble fat. A second stage is due to a slow alkaline-hydrolysis of the hemicellulose-cellulose-lignin structure with a higher hemicellulose loss proportional to alkaline-pH concentrations.

Arabinoxylan degrading enzymes include xylanases (1,4-β-D-xylan xylanohydrolase, EC 3.2.1.8) and β-xylosidases (1,4-β-D-xylan xylohydrolase, EC 3.2.1.37). The former endozyme randomly hydrolyze the insoluble and soluble xylan backbone (EC 3.2.1.8) whereas the latter exozyme hydrolyze xylose from the non-reducing end of the xylose-polymer (EC 3.2.1.37). Xylose is not usually the major product and it is typically produced after xylobiose and xylotriose (smallest oligomer). Virtually all xylanases are endo-acting as determined by chromatography or their kinetic properties (substrate and product formation), molecular weight and pH (basic or acidic) or its DNA sequence (crystal structure). They can be structurally classified into two major families or isoenzymes (F or 10 and G or 11) of glycosyl hydrolases (Jeffries, 1996). F11 xylanases are larger, with some cellulase activity and produce low DP oligosaccharides (less specific); F11 are more specific for xylan and with lower molecular weight (i.e., B. Circulans and T. harzianum).

In addition, the Enzyme Technical Association (ETA, 1999; FDA, 1998) classified as carbohydrases the following hemicellulases (trivial name): a) endoenzymes (EC 3.2.1.32=1,3-β-xylanohydrolase, 78=mannanohydrolase and 99=arabinohydrolase) and b) exoenzymes only attack branches on the xylose-polymer (pentosan), producing xylo-oligomers (EC 3.2.1.55=α-L-arabinofuranosidase, glucuronic-acid glycosilase and ferulic-acid esterase).

Currently recognized endoenzymes (xylanases) and exoenzymes produced from A. niger (EC 3.2.1.8 and 37,55), A. oryzae (EC 3.2.1.8 or 32), B.subtilis (EC 3.2.1.99), and

*Trichoderma longibrachiatum* (formerly reseei: EC 3.2.1.8) are Generally Recognized As Safe (GRAS; 21 CFR 182, 184 and 186) and require no further approval from the U.S. Food and Drug Administration or Recognized As Safe (RAS in Europe: Mathewson, 1998). However, direct and indirect food additives (i.e., packaging materials) are regulated in 21 CFR 172 and 174–178 as well. Secondary direct additives, a sub-class of direct additives, are primarily Processing Aids which are used to accomplish a technical effect during food processing but are not intended to serve a technical or as a functional additive in the finished food. They are also regulated in 21 CFR 173 (Partial List of Enzyme Preparations that are used in foods). Finally, all GRAS Substances produced through recombinant-DNA which were widely consumed prior to 1958, and which have been modified and commercially introduced after 1958 must comply with regulatory requirements proposed in 21 CFR 170.3 (GRAS Notice).

The benefits of using a commercial xylanase (endoenzyme) in cereal flours instead of a non-specific hemicellulase (endo/exoenzyme) preparation are a reduction in side activities (cellulase, beta-glucanase, protease and amylase) and a reduction of dough-stickininess. Arabinoxylan degrading enzymes with well defined endo-acting and exo-acting activities have become commercially available, for food and feed, from the following companies: Amano, Danisco-Cultor, EDC/EB, Genencor, Gist-Brocades, Iogen, Novo, Primalco, Rhodia and Rohm.

Suggested applications for commercial xylanases (endopentosanases) and hemicellulases (pentosanases) mentioned in the literature include: 1) improving the watering of spent grains and energy reduction during grain drying; 2) facilitation of dough formulation with less water, reduction of stickiness in noodle and pasta production; 3) reduction in the water content when formulating grains for flaking, puffing or extrusion; 4) retarding staling or hardening in bread; 5) relaxing dough for cookie and cracker production and use of sticky cereal flours in new product formulations; 6) increase in bran removal when added to tempering water; and 7) reducing both steeping time and starchy fiber in corn wet milling.

A moderate exoxylanase addition decreases water uptake in wheat dough, whereas using an endoxylanase increases water binding and soluble-xylans as well for a high-moisture bread product. On the contrary, if starch gelatinization is to be minimized, a higher endozyme addition is desirable and hydrolysis of the soluble fraction releases water for low-moisture cookie or cracker products (EPA Patent0/338787). Therefore, a suitable level of xylanase results in desirable dough softening without causing stickiness, thereby improving machinability during forming and baking operations.

Haarasilta et al. (U.S. Pat. No. 4,990,343) and Tanaka et al. (U.S. Pat. No. 5,698,245) have proposed that the use of hemicellulase and pentosanase (Cultor and Amano) causes decomposition of wheat insoluble fiber for bread volume increase. Van Der Wouw et al. (U.S. Pat. No. 6,066,356) also reported the use of recombinant-DNA endo-arabinoxylanase (Gist Brocades) breaks down the water-insoluble-solids (~1.5%) from degermed maize and increases their in-vitro digestion (13%–19%) for animal feed or in wheat flour for improving bread volume (~9%).

A pilot process (WO Patent 00/45647) for the preparation of a modified masa foodstuff used a reducing agent (metabisulfite) or an enzyme as a processing aid (disulfide isomerase or thiol-protease/Danisco) with masa or corn prior to nixtamalization such that the native protein is modified. Sahai and Jackson (2001) disclosed a similar process where whole-kernel corn was steeped and digested with a food-grade commercial alkaline-protease (<0.10%: 50° C.–60° C.; pH>10) which altered zein structure similarly to alkali-cooking with a partial gelatinization (~20%–40%).

A novel transgenic thermostable-reductase enzyme was cloned in corn (high-protein) mainly to enhance extractability and recovery of starch and protein important in flaking grit production and in masa production. Reduction of protein disulphide bonds alters the nature of corn flour (as a wheat substitute from high-protein corn) when steeping the corn grain between 45° C. and 95° C. instead of using sulfites. The critical steeping is required to soften the kernel and then to loosen starch granules from the complicated matrix of proteins and cell wall material that makes up the corn endosperm (WO. Patent 01/98509).

Tortilla is the main edible corn product in North and Central America. It is a flat, round, unleavened and baked thin pancake (flat-cornbread) made from fresh masa or corn dough prepared from industrial nixtamalized corn flour (masa flour). It might be mentioned that tortilla, when manually or mechanically elaborated and without additives of any kind, has a maximum shelf life of 12 to 15 hours at room temperature. Afterwards they are spoiled by microorganisms and become hard or stale (starch retrogradation) due to a physicochemical change in the starch constituent of either stored or reheated tortilla. It is known that tortillas when kept under conditions in which no moisture is lost (plastic package), nevertheless become inflexible with time and break or crumble easily when bent.

In northern South America, particularly in Colombia and Venezuela, hard endosperm corn is processed with dry milling technology without wastewater and it is further converted into a precooked, degermed and debranned flour for traditional corn foods. Its consumption is mainly in the form of "arepa", which is a flat or ovoid-shaped, unleavened, and baked thick pancake made from instant corn flour. In other South American countries, corn meal and corn flour are used for different bakery and pancake mixes as well as snack foods.

Properly processed industrial corn or masa flour simplifies the production of tortilla products, because the customer eliminates management techniques required for wastewater treatment, securing, handling and processing corn into masa for tortillas and snacks. However an instant corn flour might have the following quality and cost disadvantages: high cost, lack of flavor and poor texture in tortilla products or snacks prepared from masa flour.

Corn processors can generate added value from their industrial operations in one of three approaches: developing new products from new hybrids, increasing the yield of traditional products from corn, and improving process efficiency at a lower unit cost. In the past, this has been done by methods and using an apparatus in which the grain is cooked and/or steeped in a lime-water solution such as those disclosed in U.S. Pat. Nos. 2,584,893, 2,704,257, 3,194,664, and 4,513,018. These prior art methods for the industrial production of corn dough or masa flour involve accelerated cooking and steeping times with large amounts of solids losses (~1.5–2.5%) in the liquid waste. In addition, essential nutrients such as vitamins and some amino acids are lost, depending on the severity of the cooking, washing and drying operations.

Many and varied methods for the production of instant corn flour for food products involving reduced amounts of water with low-temperature cooking and short-time processing for a high yield of the end product have been developed, as reflected by the following U.S. Pat. Nos: 4,594,260, 5,176,931, 5,532,013, and 6,387,437. In this connection, reference is made to the following U.S. Pat. Nos: 4,594,260, 5,176,931, 5,532,013, and 6,265,013 also requiring a low-temperature drying. On the contrary, U.S. Pat. Nos: 4,513,018, 5,447,742 5,558,898, 6,068,873, 6,322,836, and 6,344,228 used a high-temperature dehydration or cooking in place of a low-temperature cooking.

Having in mind the disadvantages of the prior art methods, several studies not only have used a low-temperature precooking with minimum wastewater, but also separate corn fractions as reflected by the following U.S. Pat. Nos: 4,594,260, 5,532,013, 6,025,011, 6,068,873, 6,265,013, and 6,326,045.

A few applications for enzymatic steeping were also tested to convert a traditional masa processing with reduced wastewater into a novel biochemical process (WO Patent 00/45647 and Sahai et al., 2001) Although the above described prior art methods are capable of protease precooking or steeping whole corn for either modified masa or masa flour processing, a continuous industrial application using xylanase instead as a processing aid was still unavailable in the market at the time of the invention.

SUMMARY AND OBJECTS OF THE INVENTION

Accordingly, it is an object of this invention to provide a complete departure from the prior art accelerated precooking methods of thermal, mechanical, chemical and enzymatic or biochemical processing of whole corn in order to control starchy endosperm gelatinization without using chemicals during production of an instant corn flour for arepa and tortilla.

It is another object of this invention to use low-temperature cooking with a microbial xylanase solution for a partial hydrolysis of corn bran heteroxylans during the continuous production of precooked corn flour.

Another object is to use an industrial method and apparatus involving a low-temperature, near neutral-pH precooking which not only solubilize corn cell-walls along with a slower water diffusion effecting a controlled starch granule swelling, but also results in a reduced corn solid loss.

The above and other objects and advantages of the invention are achieved by a new continuous process applied to the production of precooked corn flour or instant corn flour for arepa and tortilla, embodiments of which include a short-time corn precooking followed by a low-temperature and near neutral-pH precooking with a xylanase as a processing aid so as to effect a partial hydrolysis of insoluble fiber and decreased gelatinization, reduced washing and corn solid loss of precooked kernel, stabilization of the moisture content to a desired optimum level for grinding, milling and drying the preconditioned kernel to produce a uniform partial gelatinization, cooling and drying the dry-ground particle, separating and recovering the fine grind so produced from the coarser grind while the latter is further aspirated to partially remove a bran fraction for feed or integral flour, remilling the isolated coarser grind and further sieving it to obtain an instant corn flour for arepa, and admixing only a fine flour with lime to produce masa flour for tortilla and derivatives thereof.

BRIEF DESCRIPTION OF THE DRAWINGS

The invention will be more fully understood from the description, which follows, and from the appended drawing in which the sole drawing FIGURE depicts an embodiment of this invention in a block-type flowchart illustrating the continuous and industrial process using a low-temperature and near neutral-pH precooking with a xylanase as a processing aid.

DETAILED DESCRIPTION OF THE PREFERRED EMBODIMENTS

Figure 1:
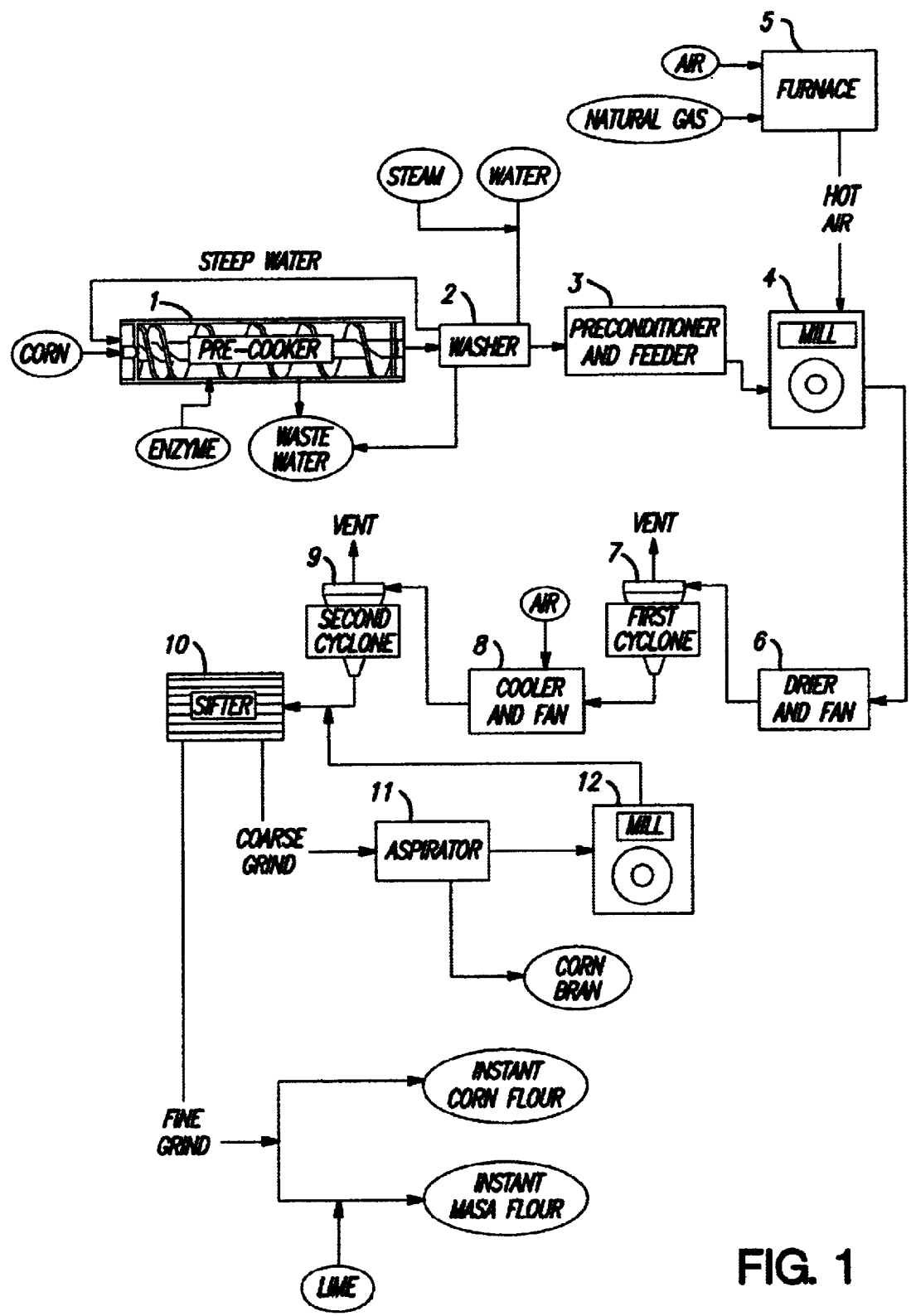

Referring first to FIG. 1, there is depicted, in flowchart form, an embodiment of the present invention. It includes a pre-cooker 1; a washer 2; a preconditioner 3 with a feeder; a primary mill 4; a furnace 5; a dryer 6 with a fan; a first cyclone separator 7; a cooler 8 with an associated fan; a second cyclone separator 9; a sifter 10; an aspirator system 11; and a secondary mill 12.

The pre-cooker 1, whose design is known per se, is fed with cleaned corn and a hot steep-water (70° C. to 85° C.) recycled from the washer 2 to form an aqueous suspension (corn to water ratio of about 1:1 to 1:1.5). The corn kernel is parboiled in order to loosen their bran cell walls and partially hydrated from a range of 9%–12% to a range of about 24%–27% for a period of about 15 to about 20 minutes. Next, a microbial xylanase solution is continuously added as a food processing aid into the pre-cooker at a low-temperature range of about 50° C. to 70° C. for another period of 15 to 75 minutes. This allows the enzymatically precooked kernel to be produced at moisture contents of between 32% and 34%, while the pH is maintained at a near neutral-pH of about 6.0 to about 7.0 with the addition of a 10% xylanase solution to supply a 0.03% to 0.07% by weight processing aid (based on corn). By controlling the steam heating along with the kernel residence time, it is possible to precook the corn at a temperature of about 50° C. to 85° C. for a total period of 30 to about 95 minutes in order to soften their bran layers.

Wastewater loss in the precooker is replaced with recycled steam-heated water from the washer 2, which is regulated to maintain the solid content of the solution from about 0.8% to about 1.1%. The industrial pre-cooker performs a partial hydrolysis of corn bran that promotes a fast water diffusion through the pericarp and tip cap layers, and later on a slow penetration via the endosperm and germ cell-walls increasing starch granule swelling. This low-temperature precooking (<70° C.) further controls the insoluble fiber solubilization (from about 0.4% to about 0.6% water-extractable solids, based on corn kernel), thus permitting a 60% reduction in soluble solids concentration as compared to the traditional alkali cooking (1%–1.6%). The partially precooked corn suspension is then passed to a washer 2 where it is sprayed with steam-heated water at a temperature of about 70° to 85° C. during 30 to 60 seconds, which also serves to increase water absorption and wash off soluble solids with denatured xylanase as wastewater.

The washed corn is thereafter passed to a preconditioner 3, where the enzymatically precooked kernel is equilibrated to obtain a residual moisture content of about 33% to about 38% for about 30 to about 150 minutes.

Thereafter, the preconditioned corn is fed through a feeder, whose design is known per se, to a primary mill 4 such that the premilled corn and hot air coming from a furnace 5, is mixed and partially cooked by an industrial dryer 6 whose design is known per se. The premilled kernel is thereby flash dried at a high-temperature from 190° C. to about 230° C. for a short time of 5 sec to about 30 sec. Its starchy endosperm is partially gelatinized or precooked to yield a moisture content of 16% to about 18% depending on the granulation being produced.

Moisture laden-hot air (110° C. to 120° C., and 11% to 13% moisture) is extracted with a first cyclone separator 7 so that further moisture extraction may take place by impelling the drier material through a cooler 8 with an associated fan, thus further decreasing the moisture content from 16–18% to about 9–12% (similar to incoming corn).

After further extraction of moisture laden-warm air (95° C. to 100° C.) with a second cyclone separator 9, the precooked dry particle is directed to a sifter 10 where the fine fraction is separated (under 20 to 60 mesh) as instant corn flour and the coarser fraction is further separated.

The latter coarse fraction is further separated in the aspirator system 11 wherein two fractions are obtained, a light-bran fraction which is isolated as feed or for integral flour with a moisture content between 9% to 12% (representing from about 3%–5% to about 6%–9% of the total weight of incoming corn), and a heavy coarser fraction that is remilled in a secondary mill 12. The milled product from secondary mill 12 is recycled to the sifter 10 for further sieving and producing a homogeneous corn flour for arepa. If desired, the arepa flour can be admixed with lime (0.3% based on precooked flour) to produce a masa flour for making tortilla or snack foods.

For use in arepa manufacture, the instant corn flour is preferably rehydrated by mixing with warm water from a 1:1.3 to about 1:1.4 weight ratio to form a corn dough (55% to 60% final moisture) for arepa elaboration.

For use in tortilla manufacture, the masa flour made from the present method can be rehydrated with water from a 1:1.0 to about 1:1.3 weight ratio for a masa dough (50% to 55% final moisture) used in tortilla or corn-based foods.

In this method, the novel enzymatic precooking results in a 45% to 55% reduction in wastewater corn solid, with correspondingly lower sewage and energy costs, as compared to the industrial methods (1.5%–2.5%). Furthermore, the enzymatic precooking of the invention allows a 50% reduction in lime use if an instant masa flour were produced to improve new flavors in corn-based foods as tostadas and snacks. The low-temperature precooking (50° C.–70° C.) at near neutral-pH (6–7) using a xylanase (0.03%–0.07%) not only aids in depolymerization of the cell-wall heteroxylans but also improves its bran removal. It also dissolves endosperm and germ cell walls facilitating a simultaneous water diffusion with a reduced gelatinization and denaturation without using a low-lime (Sahai and Jackson, 20(01, U.S. Pat. Nos.: 6,344,228 and 6,387,437) or a low-sulfite concentration (U.S. Pat. No. 6,322,836).

There is furthermore a potential in corn flour yield from 89% to 91% of the total weight of enzymatically pre-cooked corn as compared to the commercial alkali-cooking process, which yields 88%. Whereas the instant corn flour produced by the novel method may thus comprise a higher than 90% average yield of flour per kilogram of corn, the debranned and degermed flour produced by a typical arepa process obtains only a 65% to 70% yield, or a 80% to 85% yield for an integral arepa flour (U.S. Pat. No. 6,326,045).

Still further, the low-temperature and enzymatically precooked corn flour produced by the present method has a higher nutritional value as compared to the conventional methods, with more dietary fiber and fat contents than the commercial arepa or degermed corn flours (INCAP, 1961).

From the foregoing, it will be apparent that it is possible to manufacture a precooked and partially-debranned corn flour for arepa and masa flour with a novel enzymatic process which is efficient because of partial hydrolysis of cell-walls or solubilization of the endosperm periphery with starch pregelatinization and protein denaturation in the precooked corn kernel, wherein some of the nutrient losses that would have been present but for the features of this invention is prevented. The following table gives a typical nutrient average composition of Precooked flours for corn foods and traditional arepa (Cuevas, 1985):

| Nutritional profile (g/100 g): Precooked Corn Flours | | | |
|---|---|---|---|
| Nutrient | Limed-corn | Corn | Arepa |
| Water | 11.0 | 11.0 | 11.0 |
| Protein | 8.1 | 8.1 | 7.0 |
| Fat | 2.6 | 2.6 | 0.7 |
| Ash: | 1.5 | 1.3 | 0.3 |
| Calcium | 0.16 | 0.01 | 0.01 |
| Dietary fiber: | 7.0 | 7.0 | 3.0 |
| Crude fiber | 1.5 | 1.5 | 0.5 |
| Starch | 70.0 | 70.0 | 78.0 |
| Total Calories | 350 | 350 | 370 |

It is to be understood that the embodiments of this invention herein illustrated and described in detail, are by way of illustration and not of limitation. Other changes and modifications are possible and will present themselves to those skilled in the prior art and by the spirit of the appended claims.

We claim:

1. A biochemical process for the continuous production of precooked and partially debranned corn flour for arepa and tortilla, comprising the steps of:

precooking cleaned corn kernel with water heated from a downstream washer to form a suspension of corn and water, having a corn to water ratio between 1:1 and 1:1.5, precooking the corn kernel at a near neutral-pH with a solution comprising at least one xylanase, to effect a partial hydrolysis of insoluble heteroxylans or cell-walls during precooking, washing said precooked kernel to remove soluble solids and denatured xylanase, stabilizing a moisture content of said precooked corn kernel, milling said precooked washed corn kernel and drying said milled corn kernel for further pregelatinization, cooling and further drying said milled and dried corn kernel with ambient air, sifting said cooled milled corn to obtain a fine fraction, under 20 to 60 mesh to produce a corn flour with fine particle size, and a coarse fraction, aspirating said sifted coarse fraction to remove a corn bran for feed or integral flour.

2. The method of claim 1 wherein said low-temperature precooking uses a xylanase in an amount from 0.03% to about 0.07% by weight of the corn kernel.

3. The method according to claim 1 wherein said corn bran is a light fraction, representing a minimum yield from 3% to about 6% of the total weight of corn kernel.

4. The method of claim 1, wherein wastewater produced by the enzymatic precooking step comprises a corn solids reduction in a range of 45% to about 55%.

5. The method in accordance with claim 1, further comprising rehydrating said corn flour by mixing with warm water from a 1:1.3 to about 1:1.4 weight ratio to form a corn dough.

6. The method in accordance with claim 1, further comprising a step of treating said corn flour with lime to produce a masa flour.

7. The method according to claim 6, further comprising a step of rehydrating said masa flour with water from a 1:1 to about 1:1.3 weight ratio to form a masa dough.

8. The method of claim 5, wherein the corn dough has a final moisture content between 55% and 60% used in arepa preparation.

9. The method of claim 7, wherein the masa dough has a moisture in a range of 50% to 55% used in tortilla or corn-based foods.

10. The method of claim 1, wherein the hot water used in the precooking step is recycled from a downstream washer.

11. The method of claim 1, wherein the at least one xylanase is selected from microbially derived enzymes recognized as GRAS substances and processing aids.

12. The method of claim 1, wherein the low-temperature precooking step is performed up to the denaturing temperature of said xylanase.

13. The method of claim 1, wherein in the milling and drying step, the drying is performed with a high temperature-short time drier.

14. The method of claim 1, further comprising remilling the aspirated coarse fraction.

15. The method of claim 14, wherein the remilled coarser fraction is recycled to the sifting step.

* * * * *